United States Patent [19]

Matsumura

[11] 4,253,743
[45] Mar. 3, 1981

[54] EYE TESTING INSTRUMENT

[75] Inventor: Isao Matsumura, Yokosuka, Japan

[73] Assignee: Canon Kabushiki Kaisha, Tokyo, Japan

[21] Appl. No.: 902,906

[22] Filed: May 5, 1978

[30] Foreign Application Priority Data

May 17, 1977 [JP] Japan .................................. 52-56939
May 18, 1977 [JP] Japan .................................. 52-57450

[51] Int. Cl.³ .......................... A61B 3/10; A61B 3/14; G03B 29/00
[52] U.S. Cl. ................................................. 351/7; 351/6; 351/13; 354/62
[58] Field of Search ...................... 351/1, 6, 9, 13, 16, 351/39; 350/2; 356/153, 399, 400; 354/62, 165

[56] References Cited

U.S. PATENT DOCUMENTS

| | | | |
|---|---|---|---|
| 3,780,979 | 12/1973 | de Guillebon | 351/7 X |
| 3,819,256 | 6/1974 | Bellows et al. | 351/6 |
| 3,864,030 | 2/1975 | Cornsweet | 351/7 |
| 3,871,772 | 3/1975 | Munnerlyn et al. | 351/6 X |
| 3,915,564 | 10/1975 | Urban | 351/7 |
| 3,925,793 | 12/1975 | Matsumura et al. | 351/7 X |

Primary Examiner—John K. Corbin
Assistant Examiner—Rodney B. Bovernick
Attorney, Agent, or Firm—Fitzpatrick, Cella, Harper & Scinto

[57] ABSTRACT

An eye testing instrument is disclosed in which accurate aligning and spacing are obtained relative to the human eye to be tested. At least one indication mark is imaged on the cornea or iris of the eye through an objective lens of the instrument and the image of the mark is observed by the inspector. When the image of the mark appears in a predetermined position in the view field, it indicates that the instrument is in a correct position of alignment. Also, the image of the mark appears sharply and clearly whenever an accurate spacing is achieved. Therefore, the necessary adjustment of the testing instrument can be made by moving it relative to the eye backward and forward, up and down and rightward and leftward until a sharp and clear image of the indication mark appears at the predetermined position in the view field.

8 Claims, 32 Drawing Figures

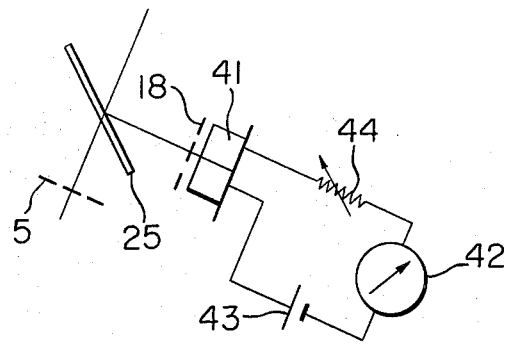
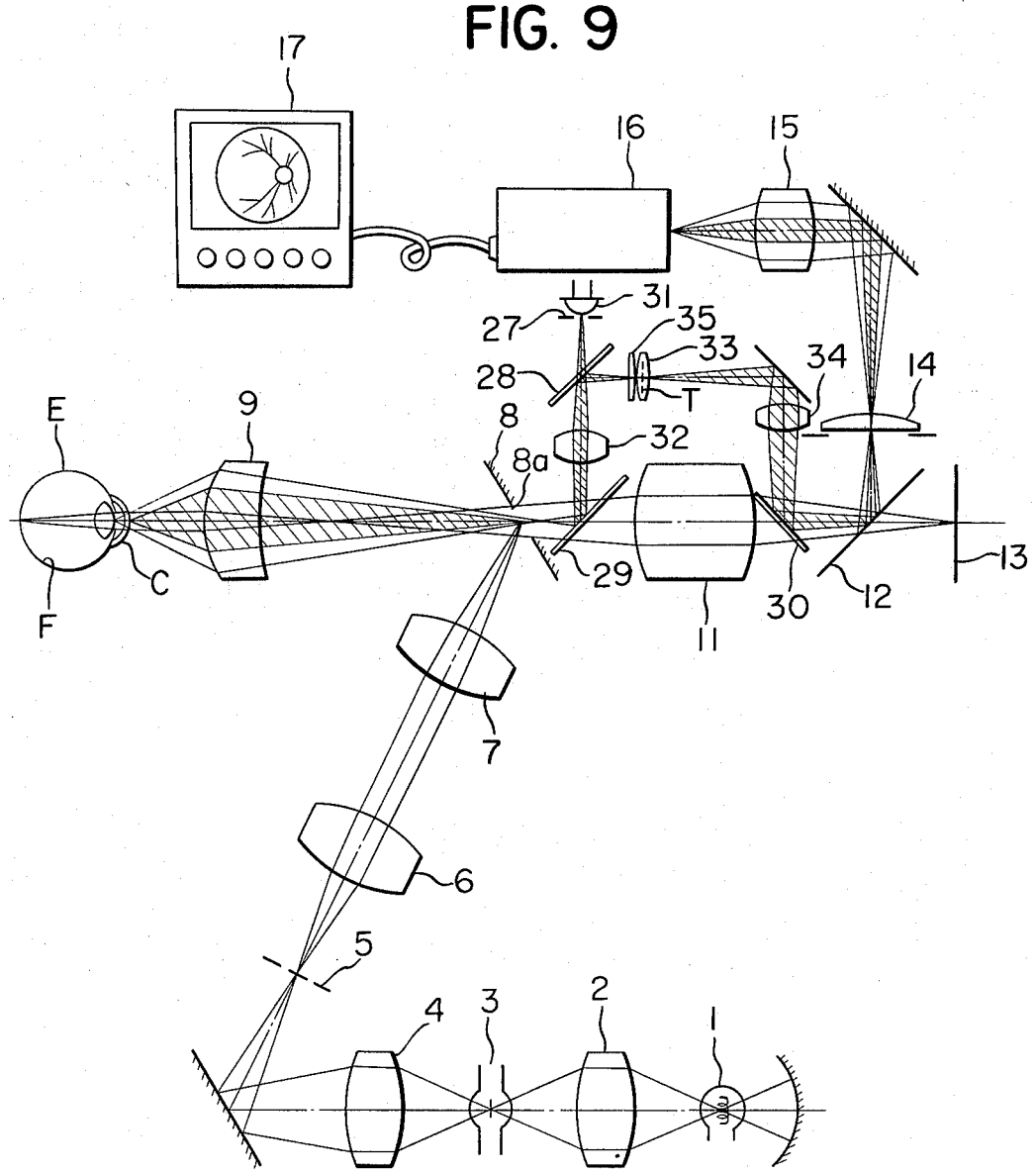

FIG. 25
FIG. 26
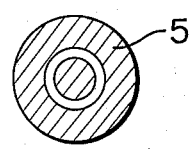
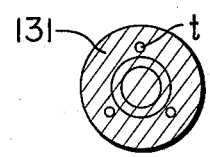
FIG. 27
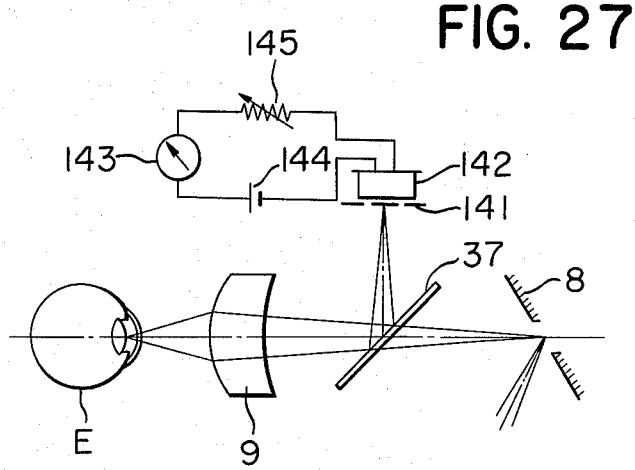
FIG. 29
FIG. 30
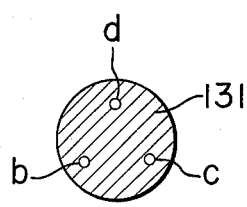
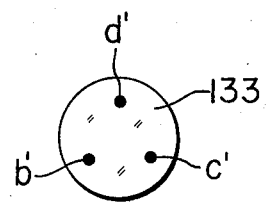
FIG. 31
FIG. 32
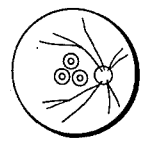
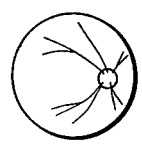

EYE TESTING INSTRUMENT

BACKGROUND OF THE INVENTION

1. Field of the Invention

The present invention relates to eye examining and testing instruments such as eye refractometers, retinoscoper and eye fundus cameras.

2. Description of the Prior Art

To effect an accurate measurement or inspection of the human eye and also to take a good picture thereof, it is of importance that the testing instrument be correctly aligned and spaced relative to the eye. If the alignment is incorrectly made, then a substantial error will be included in the obtained value of the measurement with a refractometer. Also, in case of a fundus camera, the light used for taking a picture may be adversely reflected by the iris of the eye. On the other hand, incorrect spacing will cause various problems. Usually, spacing is made by structurally predetermining the distance of a face holder on which the face of the patient is held motionless, from the objective lens of the instrument. For fundus camera, there is required a particularly accurate adjustment of the distance between the eye and the objective lens which distance is generally called the working distance. If the adjustment of working distance is incorrect, then a portion of light for illuminating the fundus may be reflected by the cornea into the picture taking light so that a flare may be produced in the image. An accurate adjustment of spacing, if attained, will greatly serve to increase the accuracy of measurement with a measuring instrument such as refractometer.

In the specification of U.S. Pat. No. 3,871,772 there is given a description of the positioning of an eye examining instrument. According to the adjustment method of alignment or spacing described therein, the anterior eye is uniformly illuminated with infrared light through an objective lens while observing the illuminated anterior eye with an aiming device supported on the body of the instrument. By aligning the center of the aiming plate with the center of the pupil of the eye to be measured, an adjustment of alignment and spacing is achieved. However, this known method has several drawbacks. In the view field of the aiming device there appears the whole anterior eye. Furthermore, the resolving power of the image is reduced because of an image intensifier incorporated into the aiming device. Therefore, it becomes very difficult for the inspector to judge whether the image of the anterior eye appearing in the view field is sufficiently sharp and clear. Thus, both the adjustments of alignment and spacing must be carried out depending only upon the positional deviation of the center of the pupil from the center of the aiming plate. This makes it impossible or very difficult to carry out the adjustment of aligning and that of spacing independently from each other.

SUMMARY OF THE INVENTION

Accordingly, it is the primary object of the present invention to make it possible to precisely adjust the working distance between a testing instrument and an eye to be tested with it.

Spacing is more difficult and therefore more important than alignment. For example, there is known such type of fundus camera which is provided, behind its objective lens, with a removal lens through which the pupil of the test eye can be observed. Alignment is relatively easy to carry out so long as the instrument is of the type which allows the examiner to observe the anterior eye through the observation system of the instrument itself. Compared with alignment, spacing is far more difficult to carry out because the detection of information of spacing adjustment is a very difficult task.

Another object of the invention is to attain a precise alignment of the test instrument with the eye.

For such type of instrument which is not provided with any observation system permitting observation of the anterior eye through it, the problem of alignment is also of importance.

A more specific object of the invention is to provide such testing instrument in which, not the anterior part of the eye, but mark or indication means is observed for the purpose of adjustment.

Still a further object of the invention is to provide observation apparatus which enables observation of both of the test object part and the mark at the same time.

Other and further objects, features and advantages of the invention will appear more fully apparent from the following description taken in connection with the accompanying drawings.

BRIEF DESCRIPTION OF THE DRAWINGS

FIG. 8 shows a modification of the embodiment;

FIG. 9 shows another embodiment of the invention;

FIGS. 11 through 14 are various illustrations of view fields displayed on the cathode-ray tube;

FIGS. 25 and 26 are detailed views of the components of the FIG. 24 embodiment;

FIG. 27 shows a partial modification of the embodiment;

FIGS. 29 and 30 are detailed views of the components of the FIG. 28 embodiment; and FIGS. 31 and 32 are images visible through the observation system of the embodiment.

DESCRIPTION OF THE PREFERRED EMBODIMENTS

Figure 1:
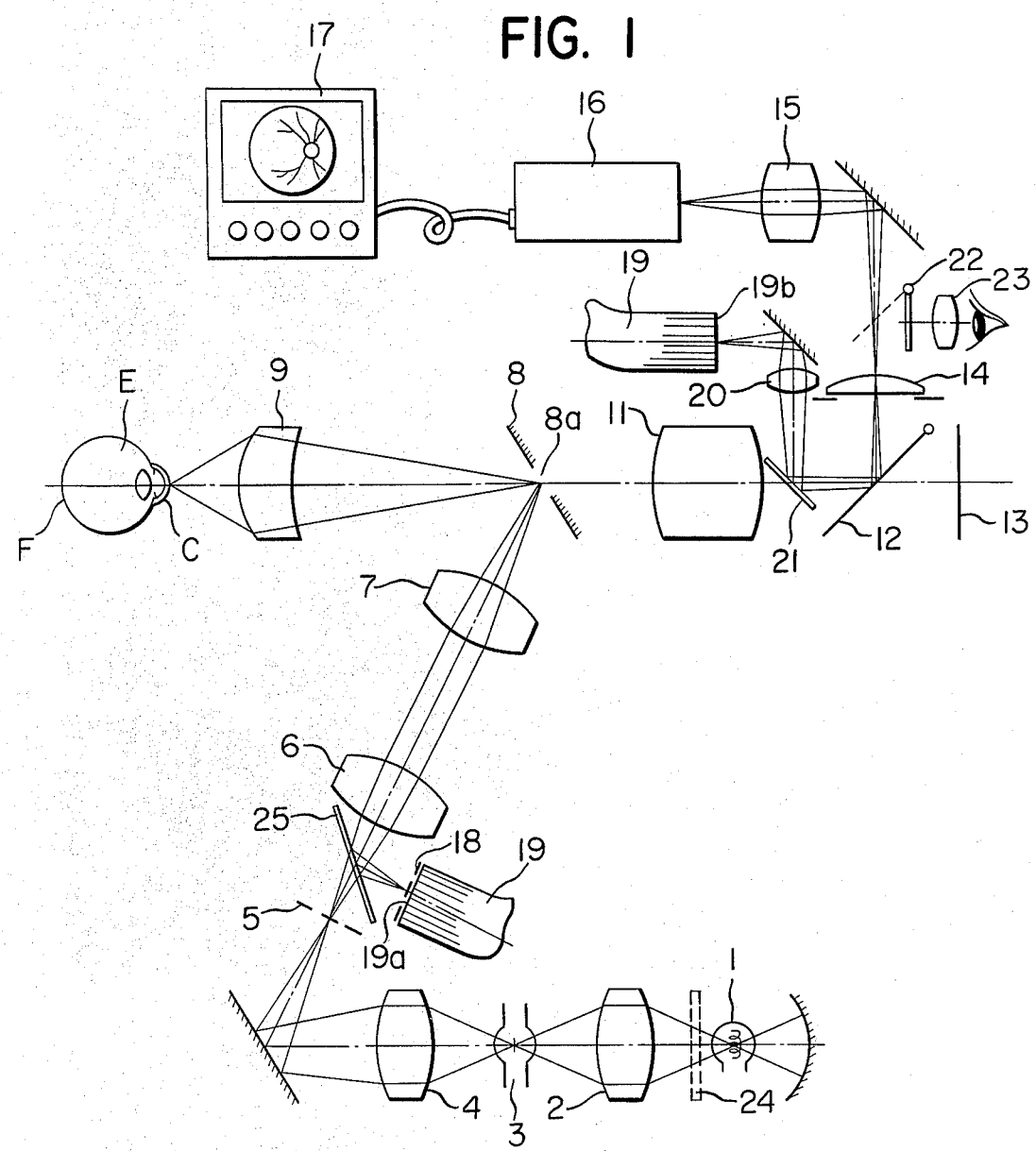
FIG. 1 schematically shows an embodiment of the invention.

Referring first to FIG. 1 there is shown a fundus camera in which the present invention is embodied. Designated by E, F and C are an eye to be tested, the fundus of the eye and the cornea of the eye, respectively. The reference numeral 1 designates a tungsten lamp, 2 is a condenser lens, 3 is a strobo tube, 4 is a condenser lens and 5 is a ring slit plate. The tungsten lamp 1 and the ring slit plate 5 are conjugate relative to the condenser lenses 2 and 4. Also, the strobo tube 3 and the ring slit plate 5 are conjugate relative to the condenser lens 4. The reference numerals 6 and 7 designate relay lenses, 8 is a mirror having an opening 8a serving also as an aperture stop and 9 is an objective lens. The aperture stop may be a separate one from the opening of the mirror. The mirror 8 and the ring slit plate 5 are conjugate relative to the relay lenses 6 and 7. Whenever the objective lens 9 for taking a picture of the fundus is in a position at which a correct working distance is obtained with respect to the eye E, the cornea C and the ring slit plate 5 have a conjugate relation relative with the relay lenses 6 and 7, the mirror surface of the bored mirror 8 and the objective lens 9. The aperture stop 8a and the cornea C of the eye E are also conjugate.

The reference numeral 11 designates an image forming lens, 12 is a jump-up mirror and 13 is a film. The lens 11 for taking a picture of the fundus forms again on the film, the image of the fundus F which was once formed by the objective lens 9. 14 is a field lens which is conjugate with the film 13 relative to the jump-up mirror 12. Designated by 15 is an image pick-up lens, 16 is a pick-up tube such as vidicon and 17 is a cathode-ray tube for monitoring. By the image pick-up lens 15, an aerial image on the field lens 14 is imaged on the light receiving surface of the vidicon 16.

In the above described arrangement, the components 1 through 9 constitute an illumination system, the components of objective lens 9, aperture stop 8, image forming lens 11 and film 13 constitute a picture taking system and the group consisting of objective lens 9, aperture stop 8, image forming lens 11, jump-up mirror 12 and other members 14 through 17 constitutes an observation system.

When there is placed in front of the tungsten lamp 1 a filter 24 which transmits infrared and near infrared rays while employing as the vidicon 16 one that is sensitive to the infrared range of light, the shown fundus camera can be used as a non-mydriatic type of fundus camera. On the contrary, when the filter 24 is removed and use is made of such a vidicon sensitive to the visible range of light or a mirror 22 disposed inclined in front of the ocular lens 23 so as to allow the observation of the fundus through the ocular lens 23, the shown fundus camera becomes a mydriatic type one.

Now, description will be made as to the projection system and the detecting system of indication mark which constitute an essential part of the invention. In the embodiment, the projection system is formed by making use of a part of the illumination system to simplify the structure of the instrument.

Figure 2:
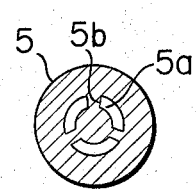
FIGS. 2 and 3 are detailed views of components of the embodiment.
Figure 3:
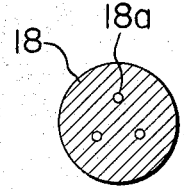
Figure 4:
FIGS. 4 and 5 are explanatory views for illustrating the optical action of the embodiment.

The member 25 disposed obliquely relative to the optical axis of the illumination system is a semi-transparent mirror (half mirror). 18 is a mask which is disposed conjugate with the ring slit plate 5 with respect to the half mirror 25. As clearly shown in FIG. 2, the ring slit plate 5 comprises a slit 5a and three stopping portions 5b. Mark 18 has three small holes 18a as best seen in FIG. 3. The position and size of these small holes 18a are measured in such manner that when the image of the stopping portions 5b is formed on the mask 18 after being projected on the cornea and reflected by it, these holes and the stopping portions imaged on the mask may overlap each other. Each small hole has preferably the same shape as that of each stopping portion. But, for the shown embodiment, these holes are in a shape of circle for the sake of easy manufacture. FIG. 4 shows the image of the slit overlapped on the mask.

Designated by 19 is a bundle of fibers the input end 19a of which is positioned close to the mask 18. In case an infrared beam is used for alignment, optical fibers for use in transmitting infrared light must be prepared.

Designated by 20 is a relay lens which makes a conjugate relation between the output end 19a of the bundle of fibers and the film 13. 21 is a half mirror which is slide movable in the direction normal to the plane of the drawing so that it may be retracted to a position outside of the light path at the time of taking a picture.

The manner of operation of the above described apparatus is as follows:

Initially, the lamp 1 and also the vidicon 16, the cathode-ray tube 17 and an electric processing circuit (not shown) are energized. The beam of light emitted from the tungsten lamp 1 is filtered by the filter 24 which transmits only infrared and near infrared rays, and therefore these rays passed through the filter are directed to the ring slit plate 5. These infrared and near infrared rays are converged on the plate 5 by the action of the condenser lenses 2 and 4 so as to illuminate the plate. The beam of infrared rays emerging from the slit 5a of the plate 5 functioning as a secondary light source for the beam once forms an image of the slit on the bored mirror 8 through the relay lenses 6 and 7, and then the infrared beam again forms the image on the cornea C through the objective lens 9. The beam also illuminates the fundus F uniformly.

Figure 5:
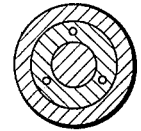

Although the cornea possesses a light scattering property to some extent, it rather functions as a mirror surface. Therefore, a portion of the infrared beam incident upon the cornea is reflected by the latter in a manner of regular reflection. The beam thus reflected enters the objective lens 9 and then converges on the bored mirror 8 which reflects the beam into the relay lens 7. Passing through the relay lenses 7 and 6 and the half mirror 25, the beam is imaged on the mask 18 or at a position in the vicinity of the mask. If a predetermined distance is correctly held between the eye E and the objective lens 9, then a clear and sharp image of the slit 5a is formed on the mask 18 as illustrated in FIG. 4. But, if the predetermined distance is not held, then the image of the slit formed on the mask becomes dim as illustrated in FIG. 5. As a result, the infrared beam passes through the small holes 18a and enters the input end of the bundle of fibers 19. The beam coming out from the output end 19b of the bundle of fibers is converged by the action of the relay lens 20, focused on the field lens 14 through the half mirror 21 and the jump-up mirror 12 and finally received by the light receiving surface of the vidicon through the image pick-up lens 15.

On the other hand, the infrared beam passed through the cornea C illuminates the fundus F and is reflected thereby. The reflected beam emerges from the eye and enters the vidicon 16 through objective lens 9, the opening 8a of mirror 8, image forming lens 11, jump-up mirror 12, field lens 14 and image pick-up lens 15.

Figure 6:
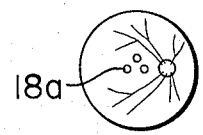
FIGS. 6 and 7 are illustrations of view fields displayed on the cathode-ray tube respectively.
Figure 7:
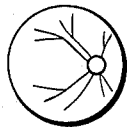

In this manner, on the screen of the cathode-ray tube 17 there appears a view as illustrated in FIG. 6 or a view as illustrated in FIG. 7. In case of FIG. 6, there are also visible light spots 18a' passed through the small holes, which indicates that the predetermined positional relation is not held between the eye and the objective lens 9. In case of FIG. 7, there is not present any image of infrared beam passed through the mask, which gives an indication that the predetermined positional relation has been satisfied. The operator can effect an alignment by moving the fundus camera in the direction of the optical axis of the objective lens until the light spots 18a' become disappear. When the optical axis of the objective lens is deviated from the center of cornea of the test eye, the light spots 18a' appear at a position deviated from the center of the visual field. Therefore, the operator can also recognize a deviation in up and down direction or in right and left direction, if any.

FIG. 8 shows a partial modification of the above described embodiment. In this modification, a photoelectric element 41 is used in place of the bundle of fibers 19 shown in FIG. 1. In FIG. 8, the reference numeral 42 designates a meter for display, 44 is a variable resistance for initial setting and 43 is a battery. These elements 41 through 44 constitute a display circuit. Since the resistance value in the display circuit varies depending upon the quantity of light incident upon the photoelectric element 41, the point of the meter deviates in accordance of the quantity of light incident upon the element 41. Therefore, the fundus camera can be adjusted to a correct working distance by moving the camera backward or forward and setting it to the position at which the deviation of the point of the meter becomes zero.

For this embodiment, adjustment of alignment is carried out as follows:

The apparatus is so constructed that the whole apparatus may be moved away from the eye E by a large distance initially. The objective lens is spaced from the eye up to the position at which the anterior eye becomes visible through the observation system. Thereafter, the operator observes the anterior eye and adjusts the apparatus in up and down direction and in left and right direction so as to align the center of the visual field and the center of the pupil of the eye. After the completion of this adjustment, the operator moves the whole apparatus forward.

FIG. 9 shows another embodiment of the invention. According to this embodiment, an indication is projected on a predetermined location lying on the extention of the optical axis of an objective lens which belongs to an ophthalmologic instrument. The operator observes an image of the indication reflected by the cornea. The degree of obscurity of the image observed gives information of the degree of deviation in longitudinal direction (forward and backward). The degree of deviation of the image from the center of visual field is indicative of the deviation of the optical axis in vertical (up and down) direction and in traverse (left and right) direction.

In FIG. 9, members and elements designated by the same reference characters and numerals as used in FIG. 1 have the same functions as in the FIG. 1 embodiment. Ring slit plate 5 used in this embodiment is provided with a ring slit the image of which is formed at the position of the pupil of the eye.

Figure 10:
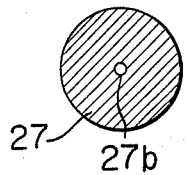
FIG. 10 is a detailed view of the component of the second embodiment.

Designated by 27 is an indication plate. As best seen in FIG. 10, the indication plate 27 has a small hole 27b at its center. The shape of the hole is not limitative. 31 is a luminescence diode disposed behind the small hole 27b. 28, 29 and 30 are half mirrors and 32 is a projection lens. The half mirror 29 is disposed at the position where the optical axis of the projection lens 32 and that of the objective lens 9 intersect. The position of the small hole 27b is so measured that the hole 27b may coincide with the optical axis of the projection lens 32 and the beam once converged by the lens may be imaged once more again by the objective lens 9 at a predetermined position. 33 is a field lens and 34 is a relay lens. The field lens 33 is positioned at T which is conjugate with the indication plate 27 relative to the half mirror 28. The relay lens 34 brings the position T and the film 13 into conjugate relation. But, the convergent beam transmitted through the relay lens 34 is concentrated on the field lens 14 through the half mirror 30 and the jump-up mirror 12. The half mirrors 29 and 30 are movably mounted and at the time of a picture being taken, these mirrors are brought into their retracted positions outside of the light path.

The manner of operation of the apparatus according to FIG. 9 embodiment is as follows:

The luminescence diode 31 is put on to illuminate the indication plate 27. The beam of light emerged from the small hole 27b is once focussed at a point in the vicinity of the opening of the mirror 8 under the action of the condenser lens 32 through the half mirror 29. Thereafter the beam is again focussed at a predetermined position lying on the extension of the optical axis through the objective lens 9. The beam by which the indication is projected is then reflected by the cornea C acting as a mirror surface. The reflected beam refractionally passes through the objective lens 9 now in the opposite direction to that in which the beam passed through it before. Then, through half mirror 29, projection lens 37, half mirror 28, field lens 33, relay lens 34, half mirror 30, jump-up mirror 12, field lens 14 and pick-up lens 15, the beam enters the vidicon 16.

On the other hand, when the tungsten lamp is on, the fundus is illuminated thereby and the light reflected upon the fundus also enters the vidicon 16 through the objective lens 9, stop 8a, image forming lens 11, jump-up mirror 12, field lens 14 and image forming lens 15.

Figure 11:
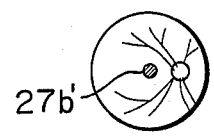

Thus, the operator observing the screen of the cathode-ray tube 17 will see a view field as illustrated in FIGS. 11 through 14. The visual field of FIG. 11 is obtained when alignment has been correctly made in all of the directions, vertical, transverse and longitudinal (along the optical axis of the objective lens) directions. The image 27b' of the small hole (indication) 27b is clear and sharp and it appears in the center of the visual field.

Figure 12:
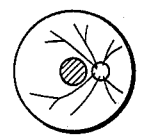

FIG. 12 illustrates a view field obtained for a case in which alignment in vertical and transverse directions has been correctly made, but there is still a deviation in longitudinal direction. In this case, the image of the indication appearing in the view field is obscure although it is seen in the center of the view field.

Figure 13:
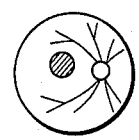

FIG. 13 illustrates a view field obtained for another case where there are deviations with respect to transverse and longitudinal directions although alignment in vertical direction is correct. The view field illustrated in FIG. 14 is for the case in which there is still a deviation in vertical direction although the alignment in transverse and longitudinal directions are correct.

The operator adjusts the position of the fundus camera while observing the image displayed on the cathode-ray tube. In the case of FIG. 12, adjustment must be done by moving the fundus camera in the longitudinal direction up to the position at which the image of the indication becomes sharp and clear. For the view field illustrated in FIG. 13, the camera must be moved at first in transverse direction so as to adjust the position of the indication to the center of the view field and then moved slightly in the longitudinal direction up to the position at which the indication image becomes clear and sharp. When a view field as illustrated in FIG. 14A is observed, an adjustment in the vertical direction is required.

In order to make it easy to ascertain the position of the image of the indication, there may be provided an aiming plate 35 disposed at a position conjugate with the indication plate 27, for example, adjacent to the field lens 33. FIG. 14B shows an example of aiming plate which is made of a transparent, flat plate having a cross described thereon.

The above described embodiments make use of the fact that the cornea of eye regularly reflects light. Now, description will be made of embodiments in which use is made of the fact that iris or sclera scatter-reflects light.

Figures 14A, 14B, 15:
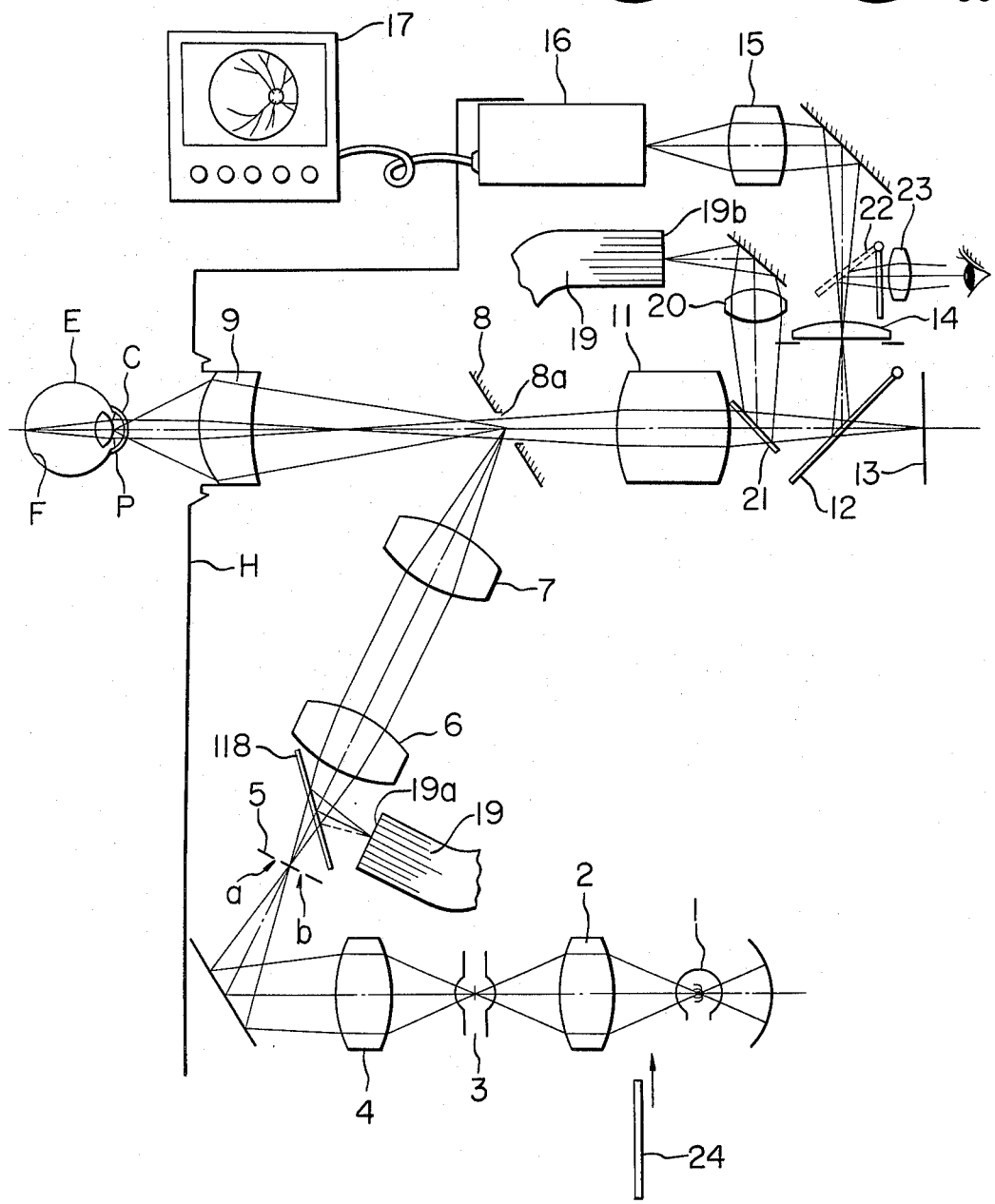
FIG. 15 shows a further embodiment of the invention.

The arrangement shown in FIG. 15 is essentially the same as that of the fundus camera shown in FIG. 1. In FIG. 15, members and elements designated by the same characters and reference numerals as used in FIG. 1 have the same functions as those in the FIG. 1 embodiment. The reference character P designates the iris of an eye E to be tested.

Designated by 118 is a half mirror, 19 is a bundle of fibers for transmitting an image and 20 is a relay lens. The input end 19a of the fiber bundle 19 and the ring slit plate 5 are conjugate relative to the half mirror 18. The output end 19b of the bundle and the film plane 13 are conjugate with respect to the relay lens 20. The reference numeral designates a half mirror disposed obliquely and mounted removably between the image forming lens 11 and the jump-up mirror 12.

Figure 16:
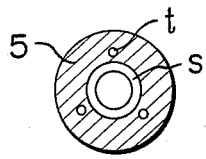
FIG. 16 is a detailed view of one component of the third embodiment.

FIG. 16 is a plan of the ring slit plate 5. The plate 5 has a single ring slit s and two or more holes t (three holes t are shown in FIG. 16). The outer diameter of the slit s is so measured that the outer circumference of the image of the slit images on the eye may be smaller than the pupil dilated by the addition of a mydriatic or may be smaller than the pupil spontaneously dilated. The position of the holes t is so measured that the point of the projection image thereof may lie on the iris P.

Figure 17:
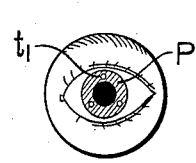
FIGS. 17 and 18 show eyes including indications projected therein respectively.

FIG. 17 illustrates the image of the small holes t projected on the eye. The image of the holes is indicated by $t_1$ and the iris by P.

The manner of operation of this embodiment is as follows: Intially, the infrared filter 24 is interposed into the light path and the tungsten lamp is put on. Also, the vidicon for infrared rays 16, cathode-ray tube 17 and a electric processing circuit (not shown) are driven. From the light emitted from the lamp 1, only infrared rays are taken up through the infrared filter 24 and converged on the ring slit plate 5 under the action of the condenser lenses 2 and 3. The infrared beam passed through the slit s and the holes t is once imaged on the bored mirror 8 under the action of relay lenses 6 and 7 and reflected upon its mirror surface. The reflected beam forms the images of the slit s and holes t respectively through the objective lens 9.

Figure 18:
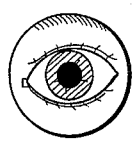

When the plane on which the image of the holes t is formed coincides with the iris P of the eye, there is produced on the iris a sharp and clear light image of the holes as illustrated in FIG. 17. On the contrary, if the distance between the objective lens 9 and the eye E is different from the value predetermined for it, an obscure light image appears as illustrated in FIG. 18.

The iris of the human eye possesses a property similar to a diffusing surface and therefore the infrared beam by which an image of the holes is formed, is reflected by the iris P in a fashion of scatter reflection. The infrared beam thus reflected on the iris enters the objective lens 9 and forms an image once on the bored mirror 8. After being reflected upon the mirror 8, the beam converges under the action of the relay lenses 7 and 6 and is imaged on the input surface 19a of the fiber bundle after reflection by the half mirror 118. Therefore, on the output surface 19a there is formed a reflection image of the holes and the infrared beam which formed the image is converged by the relay lens 20, reflected by the half mirror 21 and the jump-up mirror 12, and images on the condenser lens 14. Further, it is imaged on the vidicon 16 through the image pick-up lens 15.

On the other hand, the beam of infrared rays which forms an image of the slit at a position in the vicinity of the iris of the eye, illuminates the fundus F. After being reflected upon the fundus, the beam forms an image on the vidicon 16 through objective lens 9, the opening 8a of the bored mirror, image forming lens 11, half mirror 21, jump-up mirror 12, field lens 14 and pick-up lens 15.

Figure 22:
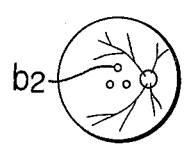
FIGS. 22 and 23 show images visible through the observation system.
Figure 23:
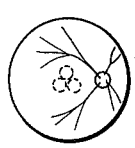

Thus, on the display screen of the cathode-ray tube 17 there appears a view field as illustrated in FIG. 22 or in FIG. 23. If the distance between the eye E and the objective lens 9 is correct, then a clear and sharp image of the three small holes t will be observed on the background of the image of the fundus as seen in FIG. 22. On the contrary, if the distance is incorrect, then the image will appear as an obscure one as illustrated in FIG. 23. In this case, an adjustment must be carried out by moving a housing H containing the optical system in the direction toward or apart from the eye up to the position at which the image b of the holes becomes clear and sharp. Mechanism for supporting the housing may be conventional and therefore it is not shown in the drawing.

Figure 19:
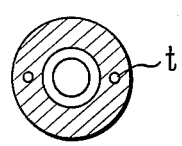
FIG. 19 is a view similar to FIG. 16 but showing a modification of the component.
Figure 20:
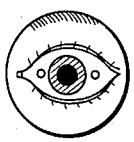
FIGS. 20 and 21 are views similar to FIGS. 17 and 18 but including indications of another form.
Figure 21:
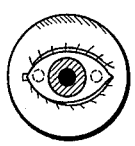

FIG. 19 shows an example of a ring slit plate adapted for projecting the holes t serving as an indication onto the sclera of the eye E. When the ring slit plate shown in FIG. 19 is used in the arrangement shown in FIG. 1 in place of the plate 5, there is formed on the sclera a sharp and clear image as illustrated in FIG. 20 or an obscure image as illustrated in FIG. 21. Accordingly, on the cathode-ray tube 17 there is displayed a clear image or an obscure image, which constitutes a measure for adjustment of working distance.

When the pupil of an eye to be tested is dilated using a mydriatic, visible range of light may be used. In this case, no contraction of the pupil is caused by the use of visible light during alignment. Therefore, the filter for infrared rays 24 is removed and instead a mirror 22 is mounted obliquely in the light path. When the tungsten lamp 1 is put on, the operator can observe a visual field as illustrated in FIG. 22 or in FIG. 23 through the ocular 23. While observing it, the operator adjusts the position of the hausing H until the image of the hole becomes clear and sharp.

Figure 24:
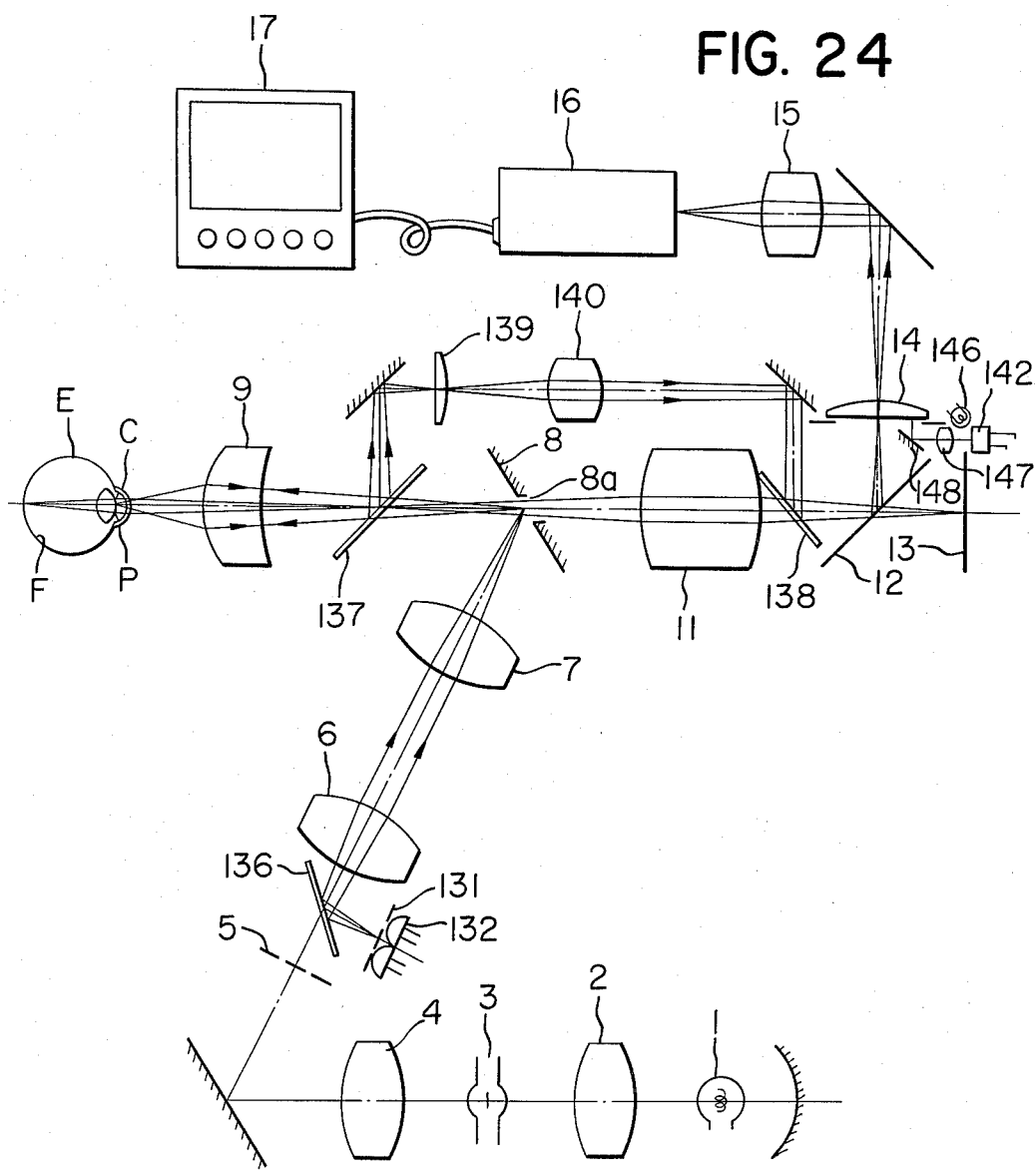
FIG. 24 shows still a further embodiment of the invention.

FIG. 24 shows still a further embodiment of the invention. Members and elements designated by the same characters and numerals as used in FIG. 15 have the same functions as in FIG. 15 embodiment. In this embodiment, the ring slit plate 5 has a ring slit only as shown in FIG. 25.

Designated by 131 is a chart plate having holes t which are projected on the iris. The chart plate and the ring slit plate are conjugate relative to the half mirror 136 serving as a beam splitter. Behind the holes of the chart plate there are disposed luminescence diodes 132 respectively as luminants. Two half mirrors 137 and 138 serve as beam splitting members. The half mirror 137 is disposed obliquely between the bored mirror 8 and the objective lens 9 whereas the half mirror 138 is disposed between the image forming lens 11 and the jump-up mirror 12. The reference numeral 139 designates a field lens which is conjugate with the position at which an image of the chart plate is formed, with respect to objective lens 9, half mirror 137 and also the deflection mirror. 140 is a relay lens by which the image of the chart plate formed on the field lens 129 is again imaged on the plane of the film. In case that the above described arrangement is used in a manner of non-mydriatic system, then such a filter which transmits infrared light and reflects visible light must be interposed between the relay lenses 6 and 7.

The manner of operation of the above described embodiment is as follows:

When the tungsten lamp 1 and luminescence diodes 132 are put on and also the vidicon 16 and the cathode-ray tube 17 are driven, there appears on the display screen a visual field as illustrated in FIG. 22 or in FIG. 23. In the first place, the light passed through the holes t provided in the chart plate 131 is reflected by the half mirror 136. The reflected light converges on the mirror surface of the bored mirror 8 through the relay lenses 6 and 7. The beam is reflected by the mirror surface and then imaged at a predetermined position through the objective lens 9. In the second place, the beam is reflected upon the iris in a fashion of scatter-reflection and directed to the objective lens going back along the light path it took before. After passing through the objective lens and then being reflected by the half mirror 137, the beam is imaged on the field lens 139 or at a position adjacent to it. Thereafter, the beam is again imaged on the image pick-up surface of the vidicon 16 through relay lens 140, half mirror 138, jump-up mirror 12, field lens 140 and pick-up lens 15.

Thus, if the image of the chart projected on the eye E coincides with the iris, then the chart is clearly and sharply displayed on the screen of the cathode-ray tube as illustrated in FIG. 22. On the contrary, if the image is formed before or after the iris, an obscure image of the chart is displayed. In the latter case, the operator can adjust the position of the objective lens 9 in the direction along the optical axis while observing the image appearing on the screen. When the strobo tube 3 is flashed to take a picture of the fundus, the half mirrors 136, 137 and 138 are retracted to their second positions out of the light path.

FIG. 27 shows a partial modification of the above described embodiment of FIG. 24. In this modification there is used a mask 141 in place of the field lens. The mask has openings corresponding to the holes t of the chart plate 131. A photo element 142, a display meter 143, a battery 144 and a variable resistor for zero adjustment 145 constitute a circuit. When the working distance is correct, the quantity of light passed through the openings of the mask 141 becomes maximum and therefore the deviation of the point of the meter becomes maximum because of the resistance of the photo element being reduced accordingly. This means that adjustment of the working distance can be achieved by moving the fundus camera forward or backward to such a position at which the deviation of the meter becomes maximum. Also, by projecting the display dial illuminated by the lamp 146 on the field lens 148 through a lens 147 and a mirror 148 as shown in FIG. 24, there is displayed the meter on the cathode-ray tube 17.

Figure 28:
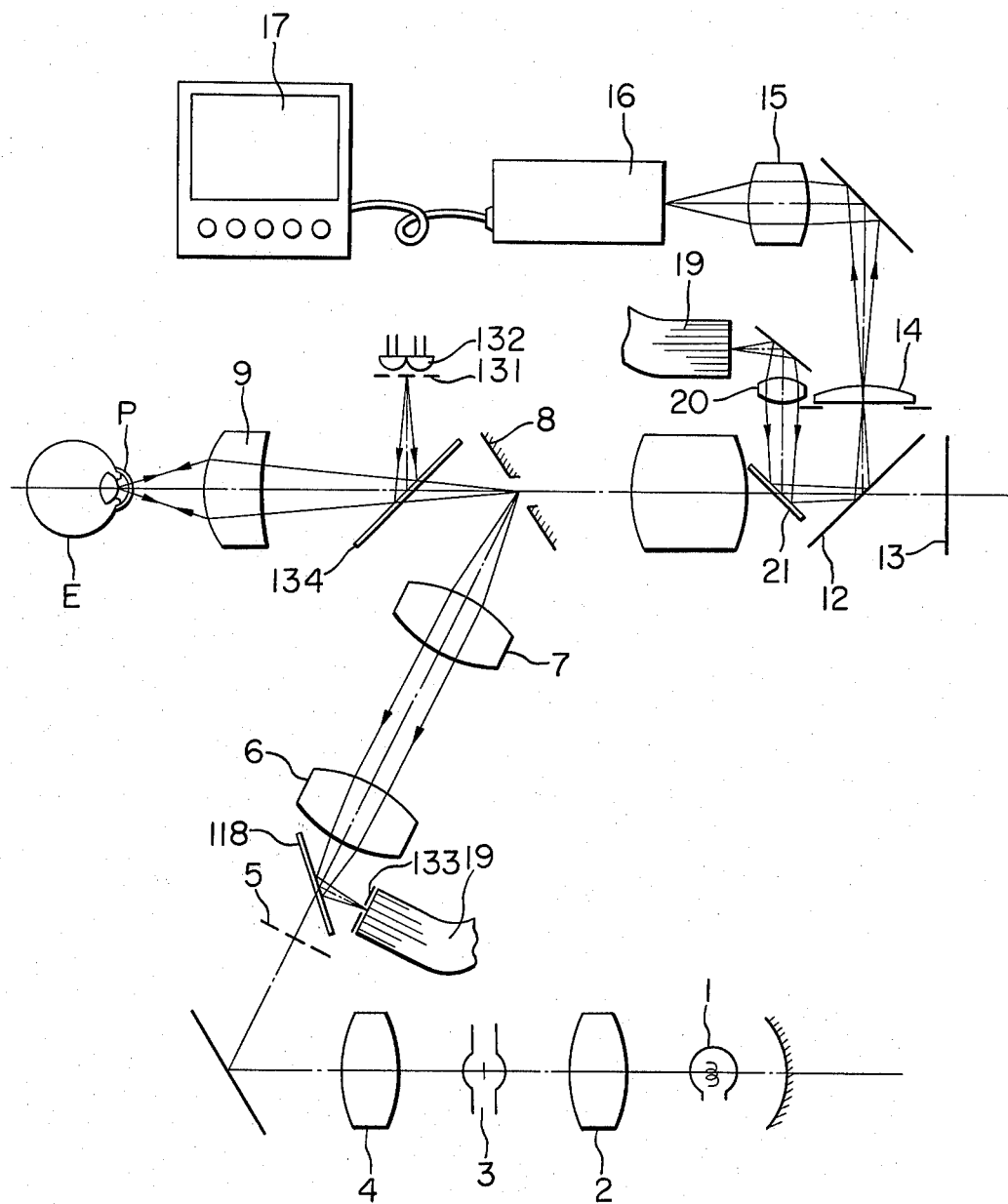
FIG. 28 shows a further embodiment of the invention.

FIG. 28 shows still a further embodiment of the invention. The same members and elements as used in the embodiment of FIG. 15 are designated by the same characters and numerals as in FIG. 15. Designated by 131 is a chart plate in which three holes b, c and d are provided. Behind the chart plate 131 there are disposed luminescence diodes 132 with each diode facing a hole. Designated by 134 is a half mirror. An image of the chart plate 131 is formed at a predetermined position through the half mirror 134 and the objective lens 9. 133 is a mask having three light stopping points b', c' and d' as shown in FIG. 30. The position and size of these stopping points are so measured that when a predetermined positional relation is held between the objective lens 9 and the eye E, these stopping points completely cover the image of the holes of the chart.

With the above described arrangement, when the luminescence diodes 132 are put on, the beam of light passed through the chart 131 is reflected by the half mirror 34, converged by the objective lens 9 and imaged at a predetermined position. The beam of light reflected upon the iris P is imaged on the bored mirror 8 through the objective lens 9 and the half mirror 134 the mirror surface of which reflects it to the relay lens 7. The reflected beam is converged by the relay lenses 7 and 6, reflected by the half mirror 18 and then imaged on the mask 133. Here, if the eye E and the objective lens hold the predetermined positional relation, then no beam of light is allowed to pass through the mask 133. But, if the distance between the eye and the objective lens is off the working distance determined therefor, then an obscure image of the chart plate will be formed on the mask 133. As a result, the light spread larger than the area of the light stopping points enters the bundle of optical fibers 19. The light emerging from the output end of the bundle 19 is incident upon the pick-up surface of the vidicon 16 through relay lens 20, half mirror 12, field lens 14 and pick-up lens 16. FIGS. 31 and 32 illustrate visual fields appearing on the screen of the cathode-ray tube 17 at this time respectively wherein the visual field illustrated in FIG. 31 is for the case in which the objective lens and the eye are out of the predetermined positional relation whereas the visual field illustrated in FIG. 32 is for the case in which the positional relation is satisfied and the image of the chart has disappeared. While the indication is observed with the background of the fundus, the beam of light illuminating the fundus may be omitted.

In place of the input end of the optical fiber bundle, a light sensitive element such as photo cell may be disposed behind the mask 133 so as to display on a meter the change of quantity of light received by the element. In such arrangement, adjustment can be attained by reducing the deviation of the meter to zero.

While the invention has been particularly shown and described with reference to preferred embodiments thereof, it will be understood by those skilled in the art that the foregoing and other changes in form and details can be made therein without departing from the spirit and scope of the invention.

What I claim is:

1. An eye testing instrument comprising:

an eye inspecting system having objective means adapted to oppose an eye to be inspected, for inspecting the eye;

a mark projecting system for projecting an image of a mark on the anterior portion of the eye spaced from said objective means a predetermined distance;

an image transmitting system for receiving the image of the mark through said objective means and transmitting the image of the mark;

an observing system, optically coupled with said image transmitting system, for observing the image of the anterior portion of the eye; and a mask positioned such that the image of said mark is not visible in the observing system in the positioning between the instrument and the eye is correct and such that the image of the mark is visible in the observing system if said positioning is not correct.

2. An eye testing instrument as claimed in claim 1, wherein said image transmitting system is a bundle of fibers.

3. An eye testing instrument as claimed in claim 1, wherein said eye inspecting system comprises a photographic system, an illuminating system and an image display system;

said imaging system comprises said objective means and a relay lens group; and said instrument further includes a detecting system comprising said image transmitting system and said image display system.

4. An eye testing instrument comprising:

objective means adapted to oppose an eye to be inspected;

an image forming lens group disposed at the image side of said objective means for forming an image of the fundus of the eye;

beam splitting means disposed between said objective means and said image forming lens group;

an illuminating system for illuminating the fundus of the eye and comprising at least one source of light, a light guiding system, said beam splitting means and said objective means;

an observing system connected with said image forming lens group for observing an image surface of said image forming lens group;

a mark projection system for projecting an image of a mark on the anterior part of the eye through said objective means masking means disposed in conjugated relationship with the anterior portion of the eye with respect to said objective means and fixed lens means, said masking means having a masking pattern corresponding to the image of the mark; and photo-detecting means positioned within said instrument so as to detect the beam which has passed through said masking means and to provide an optimum electric signal when the distance between the eye and said objective means is correct.

5. An instrument according to claim 4, further comprising, indicating means, electrically connected with said photo-detecting means, for providing visible information in said observing system.

6. An eye testing instrument comprising:

an eye photographing system for photographing the fundus of an eye to be inspected, said system including an objective lens adapted to oppose the eye, an image forming lens for cooperating with said objective lens to form an image of the eye fundus on photosensitive means, illuminating means for illuminating the eye fundus, and means for observing the imaging surface of said image forming lens;

a mark projecting system for projecting an image of a mark on the anterior part of an eye through said objective lens; and an image transmitting system, having an input surface optically conjugate with the anterior portion of the eye with respect to said objective lens, for transmitting the image of the mark to said observing means;

wherein, when the positioning between said instrument and the eye is correct, a sharp image of the mark appears in said observing means, and when the positioning is not correct, an unclear image appears therein.

7. An instrument according to claim 6, wherein said image transmitting system includes a bundle of optical fibers and two imaging lenses opposed to the ends of said bundle of optical fibers.

8. An eye testing instrument comprising, an eye examining system for examining an eye, said examining system including objective means adapted to oppose an eye to be examined, illumination means for illuminating the fundus of the eye and imaging means, disposed at the image side of said objective means, for imaging the beam reflected by the eye fundus;

a mark projecting system for directing, along the optical axis of said objective means, the beams from a mark, and forming an image of the mark on the anterior portion of the eye;

an image transmitting system, having an input surface which is optically conjugate with the anterior portion of the eye with respect to said objective means, for transmitting the image of the mark; and an observing system, optically coupled with said image transmitting means, for providing within its view field a sharp image of the mark when the positioning between said instrument and the eye is correct, and for providing therewithin an unclear image thereof when the positioning is not correct.

* * * * *

UNITED STATES PATENT AND TRADEMARK OFFICE
CERTIFICATE OF CORRECTION

PATENT NO. : 4,253,743

DATED : March 3, 1981

INVENTOR(S) : Isao Matsumura

It is certified that error appears in the above—identified patent and that said Letters Patent is hereby corrected as shown below:

Column 1, line 8, "retinoscoper" should read -- retinoscopes --.

Column 5, lines 12-13, delete "become".

Column 8, line 61, "hausing" should be -- housing --.

Signed and Sealed this

Twenty-second Day of September 1981

[SEAL]

Attest:

GERALD J. MOSSINGHOFF

Attesting Officer

Commissioner of Patents and Trademarks